(12) United States Patent
Feuerlein et al.

(10) Patent No.: US 8,509,379 B2
(45) Date of Patent: Aug. 13, 2013

(54) METHOD AND X-RAY DEVICE FOR ADAPTING GREYSCALE WINDOWING

(75) Inventors: Ute Feuerlein, Erlangen (DE); Ernst Klotz, Uttenreuth (DE); Rainer Raupach, Heroldsbach (DE); Bernhard Schmidt, Fuerth (DE)

(73) Assignee: Siemens Aktiengesellschaft, Munich (DE)

(*) Notice: Subject to any disclaimer, the term of this patent is extended or adjusted under 35 U.S.C. 154(b) by 19 days.

(21) Appl. No.: 13/360,964

(22) Filed: Jan. 30, 2012

(65) Prior Publication Data

US 2012/0201344 A1    Aug. 9, 2012

(30) Foreign Application Priority Data

Feb. 9, 2011   (DE) .......................... 10 2011 003 857

(51) Int. Cl.
*A61B 6/00*    (2006.01)
*G06K 9/00*   (2006.01)

(52) U.S. Cl.
USPC ............................................. 378/4; 382/131

(58) Field of Classification Search
USPC .......................................... 378/4, 8; 382/131
See application file for complete search history.

(56) References Cited

U.S. PATENT DOCUMENTS

| | | | | |
|---|---|---|---|---|
| 4,105,922 A | * | 8/1978 | Lambert et al. | 382/131 |
| 4,438,495 A | * | 3/1984 | Collins et al. | 382/131 |
| 5,042,077 A | * | 8/1991 | Burke | 382/169 |
| 5,058,176 A | * | 10/1991 | Shimazaki et al. | 382/132 |
| 5,305,204 A | * | 4/1994 | Ohhashi | 382/131 |
| 5,995,644 A | * | 11/1999 | Lai et al. | 382/131 |
| 6,937,767 B1 | * | 8/2005 | Burak et al. | 382/232 |
| 2004/0064038 A1 | * | 4/2004 | Bruder et al. | 600/425 |
| 2004/0066912 A1 | * | 4/2004 | Bruder et al. | 378/901 |
| 2006/0245538 A1 | | 11/2006 | Bernhardt et al. | |
| 2008/0025586 A1 | * | 1/2008 | Baumgart et al. | 382/128 |
| 2010/0014729 A1 | * | 1/2010 | Choi et al. | 382/131 |
| 2011/0317893 A1 | * | 12/2011 | Ernvik et al. | 382/128 |

OTHER PUBLICATIONS

U.S. Appl. No. 12/293,379, Nov. 10, 2011.
U.S. Appl. No. 13/293,366 Nov. 10, 2011.
"Radiation Dose and Image Quality in Pediatric CT: Effect of Technical Factors and Phantom Size and Shape," Siegel et al., Radiology, vol. 223 (2004), pp. 515-522.
"Automatic selection of tube potential for radiation dose reduction in CT: A general strategy," Yu et al., Medical Physics, vol. 37, No. 1 (2010), pp. 234-243.

* cited by examiner

*Primary Examiner* — Alexander H Taningco
(74) *Attorney, Agent, or Firm* — Schiff Hardin LLP

(57) ABSTRACT

In a method and x-ray device to adapt the width and the position of a central value of a greyscale windowing for imaging with the x-ray device based on CT values determined with said x-ray device, the adaptation takes place within the scope of a determination and adjustment of an acquisition tube voltage of an x-ray tube of the x-ray device for an examination of a defined tissue of a patient, assuming a reference tube voltage for the examination of the defined tissue of the patient, and in which a width and position of a central value of the greyscale windowing that are associated with the reference tube voltage are automatically adapted to the acquisition tube voltage.

10 Claims, 3 Drawing Sheets

METHOD AND X-RAY DEVICE FOR ADAPTING GREYSCALE WINDOWING

BACKGROUND OF THE INVENTION

1. Field of the Invention

The invention concerns a method to adapt the width and position of the central value of a greyscale windowing for imaging with an x-ray device, in particular with a computed tomography apparatus, based on CT values determined with the x-ray device. The invention also concerns an x-ray device, a computer, and a non-transitory computer readable data medium that implement such a method.

2. Description of the Prior Art

In medical engineering, in imaging with x-ray radiation, for example in computed tomography, it is always sought to apply an optimally low dose of x-ray radiation to the patient for the generation of one or more images of a tissue of the patient. A defined image quality must also be achieved, however, in order to be able to solve a clinical problem using the generated image or images, which requires a minimum dose. Relevant measures for the image quality are the image noise or the image contrast, for example. In particular, the image contrast of specific elements and materials, such as the iodine used as contrast agent in computed tomography, has a relatively strong dependency on the spectrum of the x-ray radiation that is used. Given use of relatively lower tube voltages, the spectrum of the x-ray radiation is such that the image contrast of iodine increases. Given the use of iodine, the dose of x-ray radiation that is applied to a patient to achieve an optimally high image quality depends on the spectrum of the x-ray radiation.

In CT angiography to show blood-carrying vessels, in which the visibility of iodine is of practically exclusive importance, the dose of x-ray radiation applied to the patient is therefore reduced by the use of relatively lower tube voltages (see M. J. Siegel et al., "Radiation Dose and Image Quality in Pediatric CT: Effect of Technical Factors and Phantom Size and Shape", Radiology 2004; 233: Pages 515 to 522).

In "Automatic selection of tube potential for radiation dose reduction in CT: A general strategy", L. Yu et al. propose a method to select a tube voltage suitable for a defined examination with regard to a reduction of the dose of x-ray radiation, in which an iodine contrast-to-noise ratio is used as an image quality index in connection with a noise condition a in order to be able to characterize and account for the different requirements for the image quality for different examinations. Different noise conditions a are provided for different examinations. Such a noise condition should result in the absolute image noise does not exceed a certain value. For a CT angiography in which the iodine contrast-to-noise ratio is of practically exclusive relevance, the noise condition a is chosen between 1.5 and 2.0. For breast, back or pelvic examinations with contrast agent, the noise condition a is selected between 1.1 and 1.25, and for breast, back or pelvic examinations without contrast agent the noise condition $\alpha$ is set equal to one. Based on a "relative dose factor" (RDF) (in which the contrast-to-noise ratio of iodine as well as the noise condition a are taken into account), the tube voltage is determined with which the lowest dose of x-ray radiation is applied to the patient for a specific examination.

In DE 10 2010 043 712.3 (not published prior to the filing date to which the present application is entitled), a method is described for the determination of the value of a tube voltage of an x-ray tube of an x-ray device to generate at least one image of a specific tissue of a patient that is to be examined. In this method the value of the tube voltage is determined such that upon adjustment of the value of the tube voltage at the x-ray tube and the acquisition of at least one x-ray projection of the defined tissue of the patient that is to be examined for generation of the at least one image of said defined tissue of the patient that is to be examined, the dose of x-ray radiation applied to the patient is as low as possible with consistent image quality.

The method proposed in DE 10 2010 043 712.3 (also not published prior to the filing date to which the present application is entitled) is based on the consideration that, for virtually every examination of a tissue, given a consistent image quality a tube voltage can be found at which the dose of x-ray radiation to be applied to the patient for the examination of said tissue can be reduced or optimized. The optimization thus depends on the tissue to be examined, which is to be shown in at least one image.

The starting point of this method is the consideration of the dependency of the contrast of the defined tissue to be examined (and possibly the dependency of the contrast of the defined tissue to be examined that is provided with a contrast agent) on the spectrum of the x-ray radiation of the x-ray tube, or on the value of the tube voltage that is relevant to the generated spectrum of the x-ray radiation. Furthermore, an image quality required or desired for a diagnosis, or solution to a clinical question that is intended using the at least one generated image of the defined tissue to be examined, is predetermined by at least one parameter establishing or describing the desired image quality, which can be a reference tube voltage and a reference tube current, for example, or a reference noise. Under consideration of this at least one parameter establishing or describing the image quality, and given a constantly maintained contrast-to-noise ratio, the tube voltage is determined as an image quality value, for which the dose of x-ray radiation applied to the patient is lowest in the acquisition of one or more x-ray projections to generate at least one image of the defined tissue of the patient that is to be examined.

A greyscale windowing to show the CT values based on the acquisition of x-ray projections, which CT values represent the defined tissue and tissue surrounding the defined tissue, is associated with the reference tube voltage, in which specific grey values are assigned to specific CT values. If the reference tube voltage is not used for the acquisition of the x-ray projections but rather that tube voltage at which the dose of x-ray radiation applied to the patient is lowest for the imaging of the defined tissue of the patient that is to be examined, the maintenance of the greyscale windowing that is associated with the reference tube voltage can lead to the situation that the image impression (human visual appearance) is perceived as unacceptable due to the changes of the CT values that are caused by the set tube voltage.

SUMMARY OF THE INVENTION

An object of the present invention is to provide a method, a computer-readable data storage medium, a computer, and an x-ray device of the aforementioned type wherein the image impression is optimally improved given a change of the tube voltage.

According to the invention, this object is achieved by a method to adapt the width and the position of the central value of a greyscale windowing for imaging with an x-ray device based on CT values determined with the x-ray device, the adaptation taking place within the scope of (preferably automatic) determination and adjustment of an acquisition tube voltage of an x-ray tube of the x-ray device for an examination of a defined tissue of a patient, assuming a reference tube voltage for the examination of the defined tissue of the patient, in which a width and position of the central value of the greyscale windowing, which are associated with the reference tube voltage, are automatically adapted to the acquisition tube voltage.

Due to the automatic adaptation of the greyscale windowing to the acquisition tube voltage or to the CT values modified by the acquisition tube voltage that is used in comparison to the CT values that would have resulted given use of the reference tube voltage, the original image impression remains that is familiar to the user and that was intended by the original selection or design of the greyscale windowing.

According to a variant of the invention, the width $W_{W,ref}$ of the greyscale windowing at the reference tube voltage is initially determined for the automatic adaptation of the greyscale windowing to the acquisition tube voltage.

According to a further variant of the invention, for the examination of the defined tissue, the contrast $C_{ref}$ of the defined tissue to be examined is determined at the reference tube voltage and the contrast $C_{acq}$ of the defined tissue to be examined is determined at the acquisition tube voltage.

In order to be able to determine the contrast values for the defined tissue to be examined, it is necessary to determine in advance the dependency of the contrast of various tissues that are potentially to be examined, and possibly the dependency of the contrast of various tissues to be examined that are provided with contrast agent, on the spectrum of the x-ray radiation or on the value of the tube voltage of an x-ray tube, for example by means of simulations or by means of calibration measurements. This can be done, for example using appropriately prepared phantoms, and preferably keeping these available in a data memory or database for retrieval. The dependency of the contrast of the defined tissue to be examined, and possibly the dependency of the contrast of the defined tissue to be examined that is provided with contrast agent, on the spectrum of the x-ray radiation or on the value of the tube voltage of the x-ray tube (using which the contrast can be determined for the reference tube voltage and the acquisition tube voltage, respectively) is accordingly acquired from this data memory for the respective current examination case.

According to another embodiment of the invention, a defined width $W_{fix}$ of the windowing of CT values is determined for the tissue adjacent to the defined tissue to be examined, the contrast of which has a relatively low dependency on the value of the tube voltage. The tissue adjacent to the defined tissue to be examined typically takes up no contrast agent, or only an insignificant amount of contrast agent, such that the strong dependency (due to the contrast agent) of the tissue adjacent to the defined tissue to be examined on the spectrum of the x-ray radiation, or the value of the tube voltage, does not occur. For the most part this is desirable since the tissue adjacent to the defined tissue to be examined is normally only of secondary diagnostic relevance. For example, the tissue adjacent to the defined tissue to be examined may be muscle tissue or fat tissue. Since, as already mentioned, the dependency of the contrast and the CT value of this tissue on the tube voltage is low, such that a nearly unmodified greyscale windowing is desirable for this tissue in order to keep the image impression for the tissue practically unchanged, a defined width $W_{fix}$ for the windowing of the CT values belonging to these tissues is established.

According to an embodiment of the invention, the width $W_{W,acq}$ of the greyscale windowing for the acquisition tube voltage is ultimately determined as follows:

$$W_{W,acq} = \frac{C_{acq}}{C_{ref}}(W_{W,ref} - W_{fix}) + W_{fix}$$

for $W_{W,ref} > W_{fix}$ and
$W_{W,acq} = W_{W,ref}$ otherwise.

In this manner, given a change of the tube voltage from the reference tube voltage to the acquisition tube voltage, the width $W_{W,acq}$ of the greyscale windowing for the acquisition tube voltage can be determined automatically so that the original image impression that is familiar to the user is retained. From the equation for the width $W_{W,acq}$ it is apparent that, for example in the special case for $W_{fix}=0$,—the change of the contrast for the defined tissue to be examined is entirely compensated given a switch to the acquisition tube voltage.

According to another embodiment of the invention, a central value $W_{Z,ref}$ for the greyscale windowing at the reference tube voltage is determined in order to adapt the position of the central value of a greyscale windowing at the acquisition tube voltage. For example, the central value $W_{Z,ref}$ can be the center value of the greyscale windowing for the reference tube voltage.

According to a further embodiment of the invention, the central value $W_{Z,acq}$ for the greyscale windowing at the acquisition tube voltage is determined as follows:

$$W_{Z,acq} = W_{Z,ref} + \frac{a}{2}(W_{W,acq} - W_{W,ref})$$

wherein a is a number between zero and one and allows an adjustment of the central value $W_{Z,acq}$ depending on the selection. In practice the number a can be used to update the central value for the acquisition tube voltage. In this way the grey value of a tissue that is not provided with contrast agent can effectively be kept constant as a visual reference value in the generated image, for example. a=0.75 is typical. For the special case a=0 the central value is unchanged.

The present invention also encompasses an x-ray system that is operable to implement the method described above, in any or all embodiments.

The present invention also encompasses a non-transitory, computer-readable storage medium encoded with programming instructions to implement the method described above, in any or all embodiments. When such a storage medium is loaded into a computerized control arrangement of an x-ray system, the programming instructions cause the system to implement the method described above.

DESCRIPTION OF THE PREFERRED EMBODIMENTS

Figure 1:
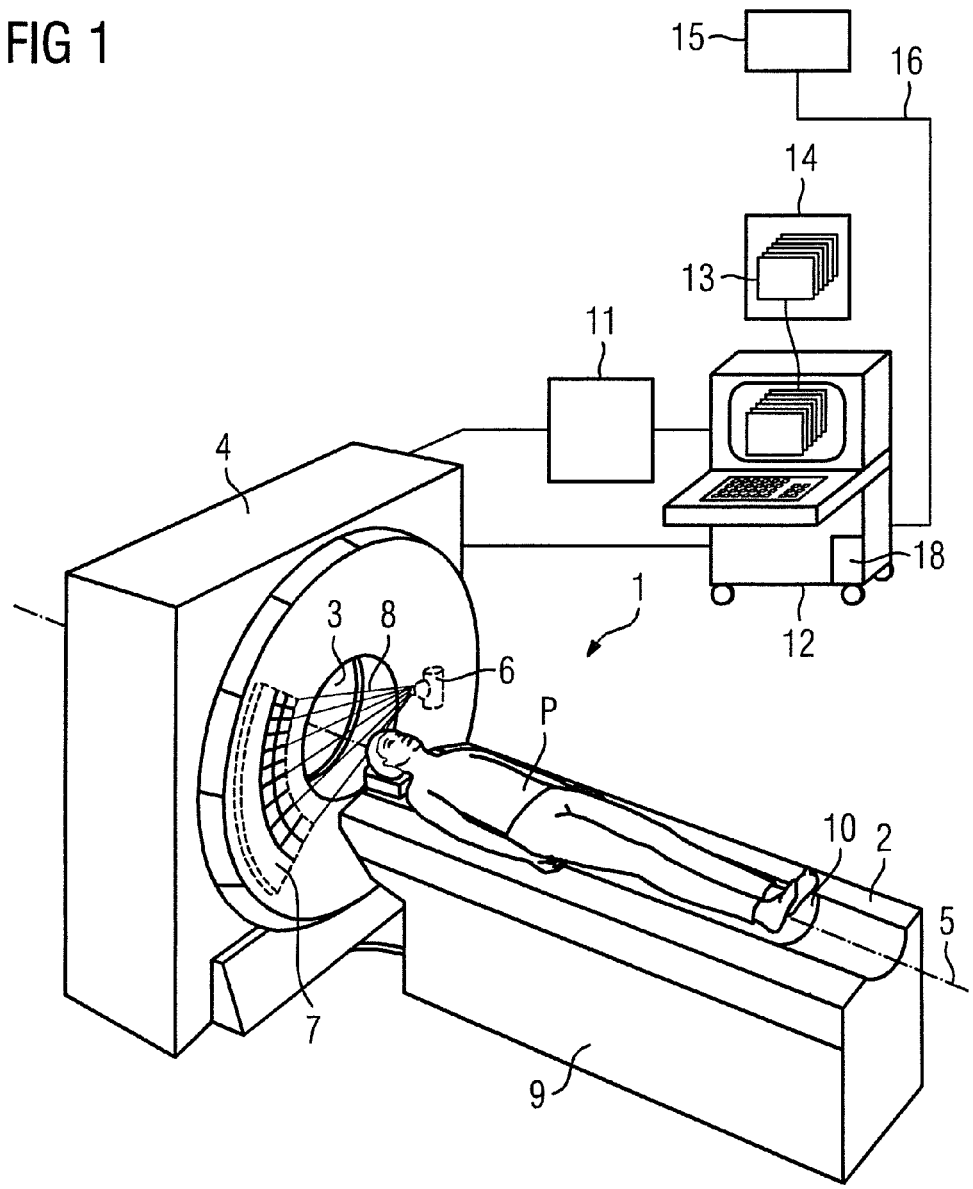
FIG. 1 schematically illustrates a computer tomography apparatus operable in accordance with the invention.

In FIG. 1 a computed tomography apparatus 1 is shown which is suitable for execution of the method according to the invention. The computed tomography apparatus 1 has a patient bed 2 to support a patient P to be examined. The computed tomography apparatus 1 also has a gantry 4 with a tube/detector system that is borne such that it can rotate around a system axis 5. The tube/detector system has an x-ray tube 6 and an x-ray detector unit 7 situated opposite one another. In operation, x-ray radiation 8 emanates from the x-ray tube 6 in the direction of the x-ray detector unit 7 and is detected by this.

The patient bed 2 has a bed base 9 on which is arranged a patient support plate 10 provided to actually support the patient P. The patient support plate 10 is adjustable relative to the bed base 9 such that said patient bearing plate 10 with the patient P can be introduced into the opening 3 of the gantry 4 to acquire x-ray projections of said patient P, for example for a topogram or in a spiral scan. The computational processing of the x-ray projections, for example the generation of a topogram, of a slice image, or the reconstruction of a volume data set of a body region or a tissue of the patient P based on the x-ray projections,—takes place with a schematically depicted image computer 11 of the computed tomography apparatus 1.

Moreover, the computer tomography apparatus 1 has a computer 12 with which computer programs can be and are executed for the operation and control of the computed tomography apparatus 1. The computer 12 does not need to be fashioned as a separate computer 12, but can be integrated into the computed tomography apparatus 1.

In the exemplary embodiment of the invention, a scan or an examination of a defined tissue (for example the liver tissue of the patient P, provided with iodine as a contrast agent) is to be implemented with the computed tomography apparatus 1. As used herein, an examination means the generation of images (slice images of the liver of the patient P in the exemplary embodiment of the invention), the evaluation of which forms the basis of a clinical diagnosis or the solution to a clinical question. For the generation of the slice images, an optimally low dose of x-ray radiation should be applied to the patient P while maintaining an image quality that is required or desired for the clinical diagnosis or the solution to the clinical question.

Starting from a reference tube voltage predetermined (as an image quality parameter establishing a desired image quality) for the examination of the liver tissue of the patient P that is provided with iodine, as is described in DE 10 2010 043 712.3 (not published prior) an acquisition tube voltage is determined based on the dependency of the contrast of the liver tissue provided with iodine on the spectrum of the x-ray radiation or on the value of the tube voltage of the x-ray tube 6, and given a contrast-to-noise ratio that is kept constant under consideration of the reference tube voltage as an image quality parameter, this determination is made such that,— given adjustment of the acquisition tube voltage at the x-ray tube 6 and the acquisition of x-ray projection of the liver tissue of the patient P that is provided with iodine for the generation of at least one slice image of said liver tissue provided with iodine, the dose of x-ray radiation that is applied to the patient P is optimally low, or as low as possible given a consistent image quality.

The correlations between image contrast and tube voltage and between image noise, tube voltage and tube current for different tissues have been determined in advance for this by means of computer simulations or calibration measurements, for example using phantoms appropriately prepared for the respective tissue. The correlations are stored in a data memory 18 of the computer 12 so that they can be retrieved. If, as in the exemplary embodiment of the invention, liver tissue provided with iodine is to be examined, the correlations mentioned in the preceding can be obtained from the data memory 18. A contrast value for the reference tube voltage can accordingly be determined using the correlation between image contrast and tube voltage for the liver tissue provided with iodine. Furthermore, using the correlation between image noise, tube voltage and tube current for the liver tissue provided with iodine, a noise value can be determined for the reference tube voltage and the associated reference tube current, which noise value establishes the contrast-to-noise ratio that is to be maintained with the determined contrast value. Given a constantly maintained contrast-to-noise ratio, the tube voltage is now varied and the tube current belonging to each tube voltage is determined from the correlation between image noise, tube voltage and tube current. Finally, the tube voltage is determined as the acquisition voltage, for which the dose of x-ray radiation that is applied to the patient is lowest in the acquisition given a consistent image quality (established by the constantly maintained contrast-to-noise ratio), based on the determined tube currents.

Due to this automatic change from the reference tube voltage to the acquisition tube voltage, however, the greyscale windowing associated with the reference tube voltage (this greyscale windowing associating specific greyscale values for the image presentation with defined CT values obtained upon adjustment of the reference tube voltage) leads to image impressions that are perceived as unacceptable by a user, since some tissues are cross-faded or are shown too dark, and thus the differentiation of tissues is made difficult or even impossible under the circumstances.

The computer 12 is therefore provided with a computer program 13 with which a greyscale windowing associated with the reference tube voltage, in particular the width and position of a central value of the greyscale windowing, can be adapted automatically to the acquisition tube voltage. The computer program 13 implements the method described in the following for adaptation of the greyscale windowing, which computer program 13 can have been loaded into the computer 12 from a portable storage medium (for example from a CD 14 or a memory stick) or from a server 15 as a data medium via a network 16.

Figure 2:
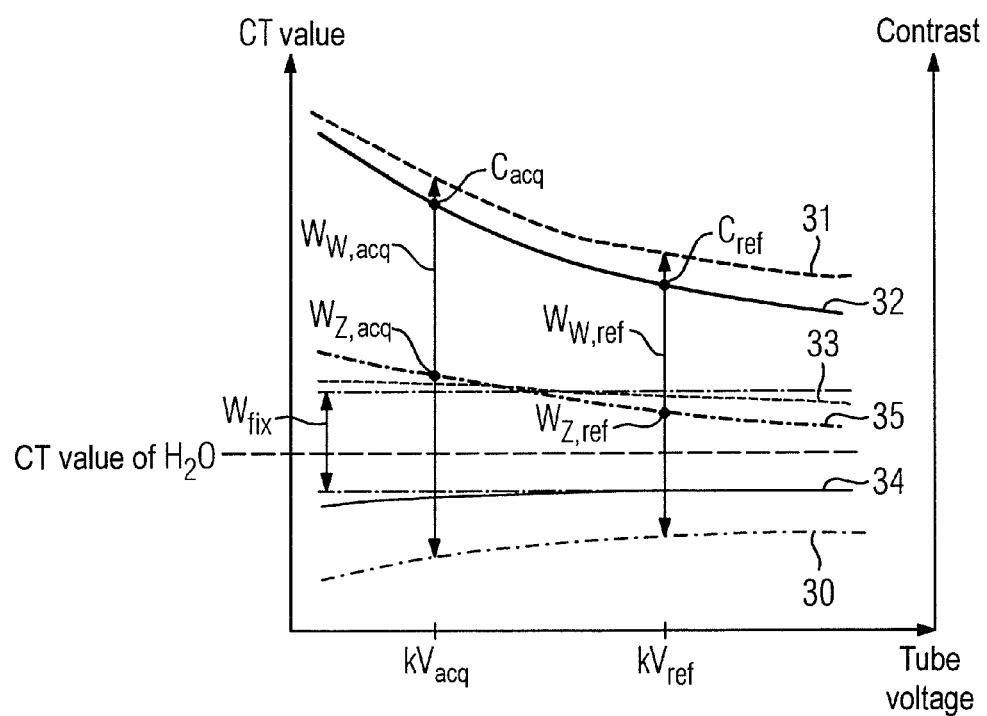
FIG. 2 is a graph illustrating the adaptation of the greyscale windowing in accordance with the invention.

The adaptation of the greyscale windowing is explained using the graph of FIG. 2. In the diagram, CT values are plotted over values for the tube voltage of the x-ray tube 6 of the computer tomography apparatus 1. The greyscale windowing across all potentially suitable tube voltages is illustrated by the curves 30 and 31. The curve 31 indicates at which CT values the grey value "black" is associated via the tube voltage, the curve 31 shows at which CT values the grey value "white" is assigned via the tube voltage. Therefore, the greyscale windowing or the greyscale window, namely the width $W_{W,ref}$ of the greyscale windowing between the grey values "black" and "white", is apparent from the graph. Furthermore, a central value $W_{Z,ref}$ is apparent from the graph for the reference tube voltage $kV_{ref}$. The central value $W_{Z,ref}$ can be (but does not have to be) the center value of the greyscale windowing.

In the graph, the dependency of the contrast on the tube voltage is also plotted for liver tissue 32 provided with iodine, for native liver tissue 33, and for fat tissue 34. From the graph it is apparent that the dependency of the contrast on the energy of the x-ray radiation or of the tube voltage, on fat tissue (as well as muscle tissue (not shown)) adjacent to the liver tissue to be examined that is provided with iodine is relatively low. Therefore, a typical bandwidth of the CT values of $W_{fix}$ is established for this tissue and for other comparable tissue, since a nearly unchanged greyscale windowing or a greyscale windowing independent of the tube voltage is desirable for this in order to keep the visual image impression constant with regard to this tissue.

Furthermore, the contrast value $C_{ref}$ of the liver tissue provided with iodine at the reference tube voltage $kV_{ref}$ and the contrast value $C_{acq}$ of the liver tissue provided with iodine at the acquisition tube voltage $kV_{ref}$ are determined. The correlation between image contrast and tube voltage for liver tissue provided with iodine (which is illustrated by the curve 32 in FIG. 2) that is present in the data memory 18 can thereby be used again.

The width $W_{W,acq}$ of the greyscale windowing or the acquisition tube voltage $kV_{acq}$ is finally determined automatically as follows by means of the computer 12:

$$W_{W,acq} = \frac{C_{acq}}{C_{ref}}(W_{W,ref} - W_{fix}) + W_{fix}$$

for $W_{W,ref} > W_{fix}$ and
$W_{W,acq} = W_{W,ref}$ otherwise.

The central value $W_{Z,acq}$ for the greyscale windowing at the acquisition tube voltage results as follows:

$$W_{Z,acq} = W_{Z,ref} + \frac{a}{2}(W_{W,acq} - W_{W,ref})$$

wherein a is a number between zero and one and allows an adjustment of the central value $W_{Z,acq}$ depending on the selection. In the diagram of FIG. 2, the curve 35 of the central values is schematically shown that—as already mentioned—can be adjusted or, respectively, modified by varying a.

Figure 3:
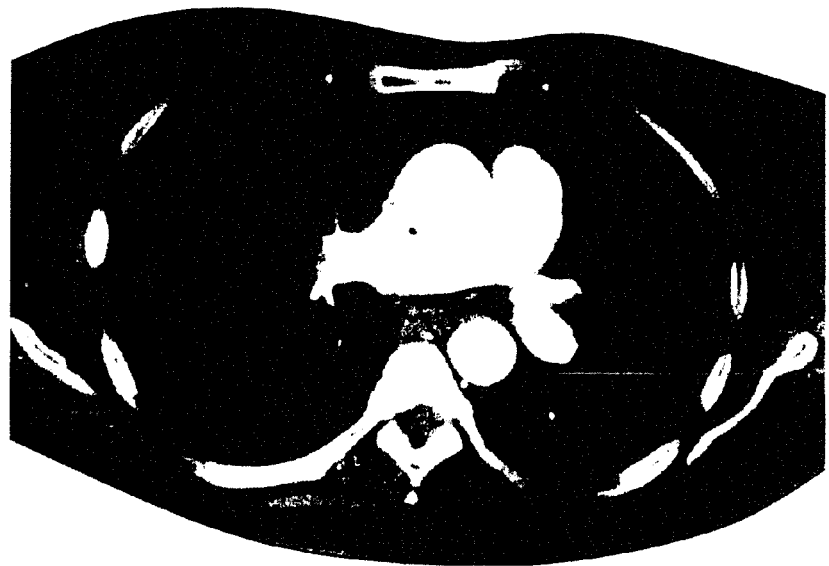
FIG. 3 shows a slice image without adaptation of the greyscale windowing.
Figure 4:
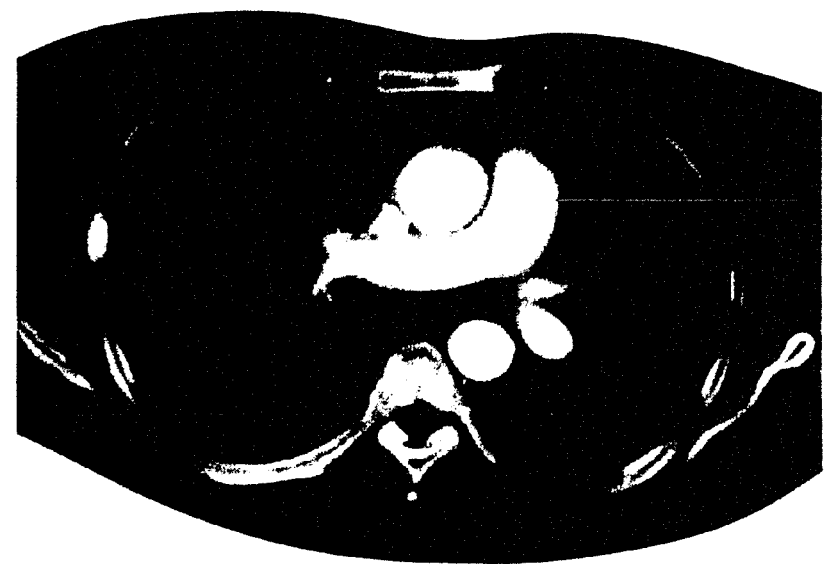
FIG. 4 shows a slice image with automatic adaptation of the greyscale windowing in accordance with the invention.

The effects of the method according to the invention are recognizable using FIGS. 3 and 4. If a switch is made from a reference tube voltage to an acquisition tube voltage without adaptation of the greyscale windowing, cross-fades that impart an unacceptable image impression can occur (as is apparent in the central image region of a slice image in FIG. 3). FIG. 4 shows the same body slice of the patient P, wherein the greyscale windowing adapted to the acquisition tube voltage was used for the generation of the slice image shown in FIG. 4, such that in particular the central image region with the customary image impression familiar to the user is shown.

In the preceding it has been explained how, after an automatic change of the tube voltage from a reference tube voltage to an acquisition tube voltage, the greyscale windowing, namely the width and the central value of the greyscale windowing, can be adapted automatically. The adaptation does not have to proceed entirely automatically. Rather, the adaptation can only be suggested to a user of the computed tomography apparatus and only be realized by a confirmation by the user, for example by this user operating a button of a graphical user interface.

Furthermore, the switch from a reference tube voltage to an acquisition tube voltage does not necessarily have to take place according to the method described in DE 10 2010 043 712.3 (not published prior). Even if the switch from a reference or initial tube voltage with which a greyscale windowing is associated to a different acquisition tube voltage is made in a different manner, the adaptation of the greyscale windowing to the acquisition tube voltage can take place automatically according to the method according to the invention.

The invention is also applicable in x-ray devices other than computed tomography systems, for example in C-arm x-ray apparatuses.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to adapt a width and a position of a central value of greyscale windowing for imaging with an x-ray device, comprising:

providing a processor with computed tomography (CT) values acquired with an x-ray device having an x-ray tube operated with an acquisition tube voltage to generate said CT values, said processor being programmed to implement a program greyscale windowing algorithm that assumes a reference tube voltage of said x-ray tube of said x-ray device and that associates a width and a position of a central value of said greyscale windowing with said reference tube voltage;

in said processor, automatically adapting said programmed greyscale windowing by automatically changing the width and the position of the central value of the greyscale windowing associated with said reference to voltage to a different width and a different position of a central value of the greyscale windowing that are associated with said acquisition tube voltage, to produce an adapted greyscale windowing algorithm; and in said processor, greyscale windowing said CT values using said adapted greyscale windowing algorithm, to generate greyscale windowed CT values, and making said greyscale windowed CT values available at an output of said processor in a form for reconstructing an image using said greyscale windowed CT values.

2. A method as claimed in claim 1 comprising, in said processor, determining the width ($W_{W,ref}$) of the greyscale windowing at the reference tube voltage.

3. A method as claimed in claim 2 comprising, in said processor, determining the contrast ($C_{ref}$) of the defined tissue to be examined at the reference tube voltage and a contrast ($C_{acq}$) of the defined tissue to be examined at the acquisition tube voltage, and using $C_{ref}$ and $C_{asq}$ to adapt said programmed greyscale windowing algorithm.

4. A method as claimed in claim 3 comprising, in said processor, establishing a defined width ($W_{fix}$) of a windowing of CT values for tissue adjacent to the defined tissue, the contrast of said adjacent tissue having a small dependency on the value of the tube voltage.

5. A method as claimed in claim 4, comprising, in said processor, determining the width ($W_{W,acq}$) of the greyscale windowing for the acquisition tube voltage as:

$$W_{W,acq} = \frac{C_{acq}}{C_{ref}}(W_{W,ref} - W_{fix}) + W_{fix}$$

for $W_{W,ref} > W_{fix}$ and
$W_{W,acq} = W_{W,ref}$ otherwise.

6. A method as claimed in claim 1 comprising, in said processor, determining a central value ($W_{Z,ref}$) for the greyscale windowing at the reference tube voltage for adaptation of the position of a central value of the greyscale windowing at the acquisition tube voltage.

7. A method as claimed in claim 6, comprising, in said processor, determining the central value ($W_{Z,acq}$) for the greyscale windowing at the acquisition tube voltage:

$$W_{Z,acq} = W_{Z,ref} + \frac{a}{2}(W_{W,acq} - W_{W,ref})$$

wherein a is a number between zero and one and allows an adjustment of the central value ($W_{Z,acq}$) depending on the selection.

8. A method as claimed in claim 1 comprising initiating said adapting of said programmed greyscale windowing algorithm by a user input entered into said processor.

9. An x-ray system comprising:
an x-ray device having an x-ray tube operated with an acquisition tube voltage to generate computer tomography (CT) values;
a processor provided with said CT values, said processor being configured to implement a program greyscale windowing algorithm that assumes a reference tube voltage of said x-ray tube of said x-ray device and that associates a width and a position of a central value of said greyscale windowing with said reference tube voltage;
said processor being configured to automatically adapt said programmed greyscale windowing by automatically changing the width and the position of the central value of the greyscale windowing associated with said reference to voltage to a different width and a different position of a central value of the greyscale windowing that are associated with said acquisition tube voltage, to produce an adapted greyscale windowing algorithm; and
said processor being configured to greyscale window said CT values using said adapted greyscale windowing algorithm, to generate greyscale windowed CT values, and to make said greyscale windowed CT values available at an output of said processor in a form for reconstructing an image using said greyscale windowed CT values.

10. A non-transitory computer-readable storage medium encoded with programming instructions for operating an x-ray system to adapt a width and a position of a central value of greyscale windowing for imaging within the x-ray device that comprises a processor in which said storage medium is loaded, said programming instructions causing said processor to:
receive computed tomography (CT) values acquired with an x-ray device having an x-ray tube operated with an acquisition tube voltage to generate said CT values, said processor being programmed to implement a program greyscale windowing algorithm that assumes a reference tube voltage of said x-ray tube of said x-ray device and that associates a width and a position of a central value of said greyscale windowing with said reference tube voltage;
automatically adapt said programmed greyscale windowing by automatically changing the width and the position of the central value of the greyscale windowing associated with said reference to voltage to a different width and a different position of a central value of the greyscale windowing that are associated with said acquisition tube voltage, to produce an adapted greyscale windowing algorithm; and
greyscale window said CT values using said adapted greyscale windowing algorithm, to generate greyscale windowed CT values, and make said greyscale windowed CT values available at an output of said processor in a form for reconstructing an image using said greyscale windowed CT values.

* * * * *